US008466127B2

(12) United States Patent
Hu et al.

(10) Patent No.: US 8,466,127 B2
(45) Date of Patent: Jun. 18, 2013

(54) PEGYLATED AND FATTY ACID GRAFTED CHITOSAN OLIGOSACCHARIDE, SYNTHESIS METHOD AND APPLICATION FOR DRUG DELIVERY SYSTEM

(75) Inventors: Fuqiang Hu, Hangzhou (CN); Yongzhong Du, Hangzhou (CN); Hong Yuan, Hangzhou (CN); Pan Meng, Hangzhou (CN)

(73) Assignee: Zhejiang University, Hangzhou (CN)

( * ) Notice: Subject to any disclaimer, the term of this patent is extended or adjusted under 35 U.S.C. 154(b) by 25 days.

(21) Appl. No.: 12/999,520

(22) PCT Filed: Jun. 16, 2009

(86) PCT No.: PCT/CN2009/000656
§ 371 (c)(1),
(2), (4) Date: Jan. 27, 2011

(87) PCT Pub. No.: WO2009/152691
PCT Pub. Date: Dec. 23, 2009

(65) Prior Publication Data
US 2011/0118200 A1     May 19, 2011

(30) Foreign Application Priority Data

Jun. 17, 2008  (CN) .......................... 2008 1 0062568

(51) Int. Cl.
| A61K 31/722 | (2006.01) |
| A61K 31/704 | (2006.01) |
| A61K 31/337 | (2006.01) |
| A61K 31/522 | (2006.01) |
| C08B 37/08  | (2006.01) |
| A61P 31/12  | (2006.01) |
| A61P 35/00  | (2006.01) |

(52) U.S. Cl.
USPC .................. 514/55; 514/54; 514/34; 514/45; 514/44 R; 536/20; 536/18.7; 435/84

(58) Field of Classification Search
USPC .................. 514/54, 34, 55, 45, 44 R; 536/20, 536/18.7; 435/84
See application file for complete search history.

(56) References Cited

U.S. PATENT DOCUMENTS

2008/0095810 A1   4/2008  Alonso Fernandez et al.

FOREIGN PATENT DOCUMENTS

| CN | 1718592 A A   | 1/2006  |
| CN | 1883708 A A   | 12/2006 |
| CN | 101148483 A A | 3/2008  |
| CN | 101254308 A A | 9/2008  |
| CN | 101293933 A   | 10/2008 |
| EP | 1 304 346 A2  | 4/2003  |
| EP | 1864653 A2    | 12/2007 |
| EP | 2 289 946 A1  | 3/2011  |
| WO | 2006/097558 A2| 9/2006  |

OTHER PUBLICATIONS

Hu et al. (European journal of pharmaceutics and biopharmaceutics: official journal of Arbeitsgemeinschaft fur Pharmazeutische Verfahrenstechnik e.V, (Nov. 2008) vol. 70, No. 3, pp. 749-757).*
S.M. Moghimi et al., "Long-Circulating and Target-Specific Nanoparticles: Theory to Practice", Pharmacological Reviews, 53(2), pp. 283-318 (2001).

(Continued)

*Primary Examiner* — Shaojia Anna Jiang
*Assistant Examiner* — Michael C Henry
(74) *Attorney, Agent, or Firm* — Edwards Wildman Palmer LLP; Jeffrey D. Hsi; Weiying Yang

(57) ABSTRACT

The present invention provides a PEGylated and fatty acid grafted chitosan oligosaccharide comprising a structural unit represented by the following Formula (I) and a structural unit represented by the following Formula (II) and synthesize method, wherein the chitosan oligosaccharide has a molecular weight of less than 200,000 Da, and a degree of deacetylation of 70%-100%, and part of free amino groups of chitosan oligosaccharide chain are replaced by a fatty acid or PEG, where n refers to degree of polymerization of the PEG, and R is an alkyl group having 11-21 carbon atoms. The grafting ratio of fatty acids is 1%-50%, and the grafting ratio of PEG is 0.05%-50%. The present invention also comprise a pharmaceutical composition comprising the PEGylated and fatty acid grafted chitosan oligosaccharide as a carrier, and use of the PEGylated and fatty acid grafted chitosan oligosaccharide in preparation of a pharmaceutical composition.

19 Claims, 3 Drawing Sheets

OTHER PUBLICATIONS

Z. Xu et al., "Study on Surface Modification and Transfection of Gene-chitosan Nanoparticles", Med. J. Nat. Defending Forces in North China, 17(1), pp. 3-5 (2005)—English Abstract.

Hai-e Xu et al., "Grafting chitosan with folic acid and poly(ethylene glycol)", Chemical Research and Application, 19(1), pp. 60-63 (2007)—English Abstract.

Hu, F.Q., et al., "*Cellular uptake and cytotoxicity of shell crosslinked stearic acid-grafted chitosan oligosaccharide micelles encapslating doxorubicin*", European Jnl. of Pharmaceutics and Biopharmaceutics, vol. 69, No. 1, May 2008, pp. 117-125.

Hu, F.Q., et al., "*Shell cross-linked stearic acid grafted chitosan oligosaccharide self-aggregated micelles for controlled release of paclitaxel*", Colloids and Surfaces, B, Biointerfaces, vol. 50, No. 2, Jul. 2006, pp. 97-103.

Casettari Luca et al., *PEGylated chitosan derivatives: Synthesis, characterization and pharmaceutical applications*, Progress in Polymer Science, vol. 37, Nov. 2011, pp. 659-685.

Extended European Search Report dated Oct. 15, 2012 issued on corresponding European Patent Application No. 09765331.5.

\* cited by examiner

PEGYLATED AND FATTY ACID GRAFTED CHITOSAN OLIGOSACCHARIDE, SYNTHESIS METHOD AND APPLICATION FOR DRUG DELIVERY SYSTEM

CROSS-REFERENCE TO RELATED APPLICATIONS

This application is the national phase under 35 U.S.C. §371 of PCT International Application No. PCT/CN2009/000656, filed on Jun. 16, 2009, which claims priority of Chinese Patent Application 200810062568.0, filed Jun. 17, 2008. The contents of each of these applications are incorporated herein by reference in their entirety.

TECHNICAL FIELD

The present invention relates to a polyethylene glycol (PEG)-modified fatty acid grafted chitosan oligosaccharide, synthesize method, pharmaceutical formulation consisting of the PEGylated fatty acid grafted chitosan oligosaccharide, and the application of the PEGylated fatty acid grafted chitosan oligosaccharide in preparation of pharmaceutical compositions.

BACKGROUND

Constrained by in vivo biological transport capability of a drug itself, it must be transported to its targets in focal tissues, focal cells and its subcellular organelles through systemic circulation depending on its physico-chemical properties to perform its efficacy. However, according to biopharmaceutics and pharmacokinetics characteristics of the existing drugs, obviously they are in lack of specificity to pathological tissue and healthy tissue. A higher dose of drug is required to achieve a satisfactory curative effect, which is prone to cause occurrence of drug toxicity/side effects, and thereby confines the clinical application of the drugs.

Targeted therapy is one of the most effective measures to solve the problems described above. Molecular targets of the drugs are mainly concentrated in cells of focal tissues, wherein enzymes account for 50%, receptors account for 35%, and ion channels account for 15%. The curative effects of the drugs are primarily implemented through occupied effect on molecular targets. For instance, the majority of molecular targets of cytotoxic anticancer drugs are DNA mainly located in the nucleus of tumor cells (such as mitomycin C, doxorubicin, camptothecin), or microtubule protein located in cytoplasm (such as paclitaxel, vinblastine). Molecular targets of gene therapy drugs are also located in the cytoplasm or nucleus of target cells, such as plasmid DNA in the nucleus, and siRNA in the cytoplasm. Molecular targets of antiviral drugs are also located in the nucleus or cytoplasm of target cells. To target a drug directly to pathological tissues (organs) and cells through an appropriate carrier technology is one of the important means to resolve the problems of low efficacy and toxicity/side effects. Currently, certain progress on targeting the antitumor drugs to tissue (organ) and cell has been made at home and abroad by carrier technologies, but no breakthrough of a curative effect has been obtained. The essence of the problem is that vast majority of molecular targets for anticancer drugs are located within cells. Therefore, research and development on the materials of drug carriers targeting to molecular target points (subcellular organelles) within tumor cells is the key to break the bottleneck of cancer chemotherapy.

Design of a targeting carrier is mainly involved in targeting effect of the carrier to focal organs and targeting effect of focal cells across focal organs based thereon, so as to achieve the targeting effect to subcellular organelles for a drug molecular target. In the early targeting of drugs to tissues and organs, a small particle size of particulates is used to passive target to organs, such as liver, and a concentration on tumor tissues is achieved through an enhanced permeability and retention effect.

Currently, based on overexpression characteristics of certain receptors on tumor cell surface (such as the folate receptor), ligand-modified carrier materials have been successfully applied in targeted cancer therapy to achieve targeting to tumor cells, improve the intracellular concentration of anti-cancer drugs and enhance the efficacy of anticancer drugs themselves. Recently, polymer micelles have attracted an extensive attention in the fields of pharmaceutics, and bio-medicine. Polymer micelles are formed of amphiphilic block copolymers or graft copolymers in an aqueous media by self-assembly, and have a core-shell structure. In the polymer micelle, hydrophobic segments and hydrophilic segments form the core and shell of the micelle, respectively. The hydrophobic core can serve as a poorly water soluble drug. The outer hydrophilic membrane maintains stability of the micelle in an aqueous environment, and may modify the physical and chemical properties to achieve particular purposes, such as, active targeting effect of the micelle.

The polymer micelle as a drug delivery system has many advantages. It can control in vivo release of drugs by regulating properties of the material, such as, solubility, pH value, zeta potential and the like. Since the particle size of the micelle is rather small, it can not only permeate through blood-brain barrier and reticuloendothelial system, but also promote absorption of gastrointestinal mucosa and the like, so as to reach the location where large-size particles can not pass through, thereby achieving the purpose of a passive targeting. A protection and shielding effect of the polymer micelle skeleton can prevent the drug from being decomposed to some extent, maintain stability of the drug and reduce toxicity of the drug. In comparison to liposomes, drug loading of the polymer micelle is relatively higher. Diversity of the polymer materials is in favor of production of diversified pharmaceutical preparations using the polymer as a carrier, thereby meeting requirements of various applications.

It has been reported that a hydrophilic PEGylation of a drug carrier can reduce both plasma protein adsorption on the carrier and phagocytosis of the drug carrier by macrophage, thereby prolonging half-life of the carrier in the circulatory system. On this basis, a PEGylation of the hydrophilic shell for polymer micelles can reduce opsonification of plasma protein of polymer micelles, thereby reducing the uptake of polymer micelles by macrophage and postponing elimination of polymer micelles from the plasma. The passive targeting of polymer micelles in tumor tissue can be further improved through the enhanced permeability and retention effect. On the other hand, an active targeting to other organs and tissues can be implemented by a ligand- or antibody-modification.

In the present invention, on the basis of our previous study, a fatty acid grafted chitosan oligosaccharide micelle having rapid cellular uptake and organelle targeting effect has been employed to carry out a surface modification with PEG to synthesize a long-circulating fatty acid grafted chitosan oligosaccharide which can avoid identification of reticuloendothelial system. Such a fatty acid grafted chitosan oligosaccharide can be applied to preparation and application of anticancer drugs, gene therapy drugs, antiviral drugs and so on.

SUMMARY OF THE INVENTION

In order to improve in vivo targeting and absorption of an pharmaceutically active ingredient, the present invention provides a PEGylated and fatty acid grafted chitosan oligosaccharide, which can control in vivo release of a pharmaceutically active ingredient by forming polymer micelles, and achieve active and passive drug targeting, prevent the drug from be decomposed to some extent, maintain stability of the drug, and reduce toxicity/side effects of the drug. The PEGylated fatty acid grafted chitosan oligosaccharide can be applied as a drug carrier in the preparation of various drugs, such as, anticancer drugs, gene therapy drugs, drugs and the like.

The PEGylated fatty acid grafted chitosan oligosaccharide of the present invention may comprise a structural unit represented by the following Formula (I) and a structural unit represented by the following Formula (II), wherein part of free amino groups of chitosan oligosaccharide chain are replaced by a fatty acid having 12-22 carbon atoms or a PEG having a molecular weight of 1,000-10,000. In the formulas, n refers to polymerization degree of the PEG, and R is an alkyl group having 11-21 carbon atoms.

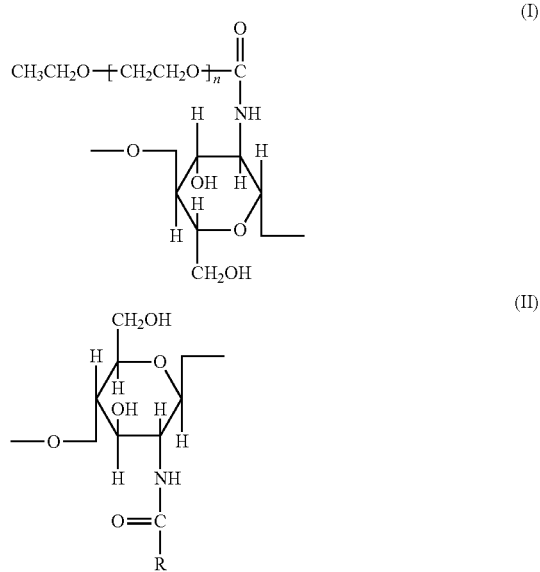

In the PEGylated fatty acid grafted chitosan oligosaccharide of the present invention, the grafting ratio of fatty acids is 1%-50%, and the grafting ratio of PEG is 0.05%-50%.

The fatty acid grafted chitosan oligosaccharide refers to an oligomer in which part of free amino groups in the chitosan oligosaccharide chain are replaced by a fatty acid. The fatty acid can be a saturated or unsaturated fatty acid having 12-22 carbon atoms. On the other hand, the fatty acid can also be straight or branched fatty acid having 12-22 carbon atoms. In addition, the fatty acid preferably has 12-20 carbon atoms, or 12-18 carbon atoms, or 14-22 carbon atoms, or 16-22 carbon atoms, or 14-20 carbon atoms, or 16-18 carbon atoms. Preferably, the fatty acid can be selected from lauric acid, myristic acid, palmitic acid, oleic acid, stearic acid, docosanoic acid or any mixture of them.

The chitosan oligosaccharide used in the present invention can be obtained by degrading a chitosan wherein N-acetyl glucosamine or glucosamine is linked through a β-1,4-glycosidic linkage. For instance, the chitosan oligosaccharide can be those having a molecular weight of less than 200,000 and a degree of deacetylation of 70%-100%. Preferably, the degree of deacetylation of the chitosan oligosaccharide can be 80%-100%, of which, 90%-100% is preferable, and it also can be 70%-80% or 70%-90%.

The chitosan oligosaccharide used in the present invention preferably has a molecular weight of less than 100,000, more preferably less than 50,000, and most preferably less than 5,000. On the other hand, the chitosan oligosaccharide used in the present invention preferably has a molecular weight of greater than 500, more preferably greater than 1,000, and most preferably greater than 2,000. For example, the molecular weight of chitosan oligosaccharide can be 500-100,000, 500-50,000, 500-5000, 1,000-100,000, 2,000-100,000, 1,000-50,000 or 2,000-5,000.

In the PEGylated fatty acid grafted chitosan oligosaccharide of the present invention, the grafting ratio of fatty acids is greater than or equal to 1%, preferably greater than or equal to 5%, more preferably greater than or equal to 10%, still more preferably greater than or equal to 15%, and most preferably greater than or equal to 20%. On the other hand, the grafting ratio of fatty acid is less than or equal to 50%, preferably less than or equal to 45%, more preferably less than or equal to 40%, still more preferably less than or equal to 35%, most preferably less than or equal to 30%. For example, the grafting ratio of fatty acids can be 1%-50%, 5%-50%, 10%-50%, 15%-50%, 20%-50%, 1%-45%, 1%-40%, 1%-35%, 1%-30%, 5%-45%, 10%-40%, 15%-35% or 20%-30%.

In the PEGylated fatty acid grafted chitosan oligosaccharide of the present invention, the grafting ratio of PEG is greater than or equal to 0.05%, preferably greater than or equal to 0.1%, more preferably greater than or equal to 1.0%, still more preferably greater than or equal to 5.0%, and most preferably greater than or equal to 10.0%. On the other hand, the grafting ratio of PEG is less than or equal to 50%, preferably less than or equal to 45%, more preferably less than or equal to 40%, still more preferably less than or equal to 35%, and most preferably less than or equal to 30%. For example, the grafting ratio of PEG can be 0.05%-50%, 0.5%-50%, 1.0%-50%, 5.0%-50% 10.0%-50% 0.1%-45%, 0.1%-40%, 0.1%-35%, 0.1%-30%, 0.5%-45%, 1.0%-40%, 5.0%-35% or 10.0%-30%.

In the PEGylated fatty acid grafted chitosan oligosaccharide of the present invention, the molecular weight of PEG is greater than or equal to 1,000, preferably greater than or equal to 1,500, more preferably greater than or equal to 2,000, still more preferably greater than or equal to 2,500, and most preferably greater than or equal to 3,000. On the other hand, the molecular weight of PEG is less than or equal to 10,000, preferably less than or equal to 9,500, more preferably less than or equal to 9,000, still more preferably less than or equal to 8,000, and most preferably less than or equal to 7,000. For instance, the molecular weight of PEG can be 1,000-10,000, 1,500-10,000, 2,000-10,000, 2,500-10,000, 3,000-10,000, 1,000-9,500, 1,000-9,000, 1,000-8,000, 1,000-7,000, 1,500-9,500, 2,000-9,000, 2,500-8,000 or 3,000-7,000.

The PEGylated fatty acid grafted chitosan oligosaccharide of the present invention can be prepared by modifying a fatty acid grafted chitosan oligosaccharide with PEG. A typical preparation method can comprise the following steps:

(a) degrading a chitosan in the presence of an enzyme to obtain a chitosan oligosaccharide having a molecular weight of less than 200,000;

(b) coupling the chitosan oligosaccharide with a fatty acid having 12-22 carbon atoms in the presence of a crosslinking coupling agent to obtain a fatty acid grafted chitosan oligosaccharide;

(c) coupling a terminal-substituted PEG with the fatty acid grafted chitosan oligosaccharide to obtain the PEGylated and fatty acid grafted chitosan oligosaccharide, wherein the molecular weight of the PEG is 1,000-10,000.

In the above steps (a), degradation of the chitosan can be carried out by a method well-known in the art. For example, the enzyme used during the degradation can be a cellulase. Moreover, the weight ratio of the enzyme to chitosan can be 0.05-5.0:100. The degradation can be carried out at a temperature 50-65° C. and a pH value 4.0-6.0. After completion of the degradation, a separation or purification can be carried out by a method well-known in the art. For example, an ultrafiltration membrane can be used for ultrafiltration, and the resultant filtrate is freeze-dried to obtain a chitosan oligosaccharide having a molecular weight of less than 200,000.

In the above step (b), the coupling of chitosan and fatty acid can be carried out by a method well-known in the art. For instance, the crosslinking coupling agent used in the step can be any of those well-known in the art, such as, 1-hydroxybenzotriazole (abbreviated as HOBT), benzotriazol-1-yloxy-tris (dimethylamino)-phosphonium hexafluorophosphate (abbreviated as BOP), N,N'-dicyclohexylcarbodiimide (abbreviated as DCC), 1-ethyl-3-(3-dimethylaminopropyl) carbodiimide (abbreviated as EDC) or the like. In addition, the molar ratio of chitosan, fatty acid and crosslinking coupling agent can be 1:1-50:1-50. The coupling of chitosan and fatty acids can be carried out at a temperature of 4-90° C. After completion of the coupling, a separation or purification can be carried out by a method well-known in the art. For example, the coupling reaction solution can be purified by dialysis, and then is freeze-dried to obtain a hydrophobic modified chitosan oligosaccharide, i.e., the fatty acid grafted chitosan oligosaccharide.

In the above step (c), the terminal-substituted PEG can be any terminal-activated PEG which can be coupled with the fatty acid grafted chitosan oligosaccharide obtained in the above step (b) through a proper reaction, such as, terminal-aldehydated group-PEG, terminal-carboxylated PEG, and terminal succinimidated-PEG, terminal-maleic anhydridated-PEG or the like. In the step (c), the molar ratio of the terminal-substituted PEG to the fatty acid grafted chitosan oligosaccharide obtained in the above step (b) can be 1:20-80:1. In one aspect, such a ratio can preferably be 1:20-1:1, more preferably 1:5-5:1, still more preferably 1:5-10:1, further more preferably 1:5-20:1, and most preferably 1:5-50:1. On the other hand, the ratio can be preferably 50:1-80:1, more preferably 20:1-80:1, still more preferably 10:1-80:1, further more preferably 10:1-80:1, and most preferably 5:1-80:1. More preferably, the ratio can be 1:1-50:1, 5:1-20:1, or 10:1-20:1. For instance, in the step (c), the molar ratio of the terminal-substituted PEG to the chitosan oligosaccharide fatty acid graft can be 1:20, 1:10, 1:5, 1:1, 5:1, 10:1, 20:1, 50:1, 80:1 or any other appropriate ratio.

In the step (c), the coupling can be carried out through a Schiff reaction between terminal active groups of PEG and amino groups of the fatty acid grafted chitosan oligosaccharide. For instance, in the case of terminal-aldehydated PEG, the coupling can be carried out through a Schiff reaction between the terminal aldehyde group of PEG and amino groups. As known in the art, during the above-mentioned Schiff reaction, a mixture of reactants and water can be subjected to ultrasound to promote the dissolution, and can be stirred at the room temperature. After completion of the reaction, a separation or purification can be carried out by a method well-known in the art. For example, the coupling reaction solution can be purified by dialysis, and then is freeze-dried to obtain the PEGylated and fatty acid grafted chitosan oligosaccharide.

In addition, the coupling can be carried out through a condensation reaction between terminal active groups of PEG and amino groups of the fatty acid grafted chitosan oligosaccharide. For instance, in the case of terminal-succinimidated PEG or terminal-maleic anhydridated PEG, the coupling can be carried out through a condensation reaction between the terminal succinimide or maleic anhydride group of PEG and amino groups. In the case of terminal-aldehydated PEG, the reaction can be carried out in the presence of an appropriate condensing agent, such as, 1-hydroxybenzotriazole (abbreviated as HOBT), benzotriazol-1-yloxy-tris (dimethylamino)-phosphonium hexafluorophosphate (abbreviated as BOP), N,N'-Dicyclohexylcarbodiimide (abbreviated as DCC), 1-ethyl-3-(3-dimethylaminopropyl) carbodiimide (abbreviated as EDC) and the like. After completion of the condensation reaction, a separation or purification can be carried out by a method well-known in the art. For example, the coupling reaction solution can be purified by dialysis, and then is freeze-dried to obtain the PEGylated and fatty acid grafted chitosan oligosaccharide.

The PEGylated and fatty acid grafted chitosan oligosaccharide of the present invention has the ability to form micelles by self-assembly in an aqueous media. For example, the PEGylated and fatty acid grafted chitosan oligosaccharide of the present invention in a concentration of 1.0 mg/mL can form micelles in water or in a buffer having a pH value of 1-12. As measure by a particle size analyzer, the particle diameter of the aforesaid micelles ranges from 20 to 500 nm. As measured by a surface potential analyzer, the surface potential of the aforesaid micelles ranges from 10 to 50 mV. As measured by the pyrene fluorescence method, the critical micelle concentration (CMC) of the PEGylated and fatty acid grafted chitosan oligosaccharide of the present invention in PBS ranges from 5 to 300 µg/mL.

The present invention also provides a pharmaceutical composition comprising the above-mentioned PEGylated and fatty acid grafted chitosan oligosaccharide as a carrier. The pharmaceutical composition can comprise an appropriate pharmaceutically active ingredient and the PEGylated and fatty acid grafted chitosan oligosaccharide of the invention.

In the pharmaceutical composition of the present invention, the pharmaceutically active ingredient can be an antitumor drug, such as, mitomycin C, doxorubicin, paclitaxel, hydroxycamptothecin (HCPT) or the like. The antitumor pharmaceutical composition of the present invention can reverse drug resistance of tumor cells.

In the pharmaceutical composition of the present invention, the pharmaceutically active ingredient can be a gene therapy drug, such as, plasmid DNA, siRNA or the like.

In the pharmaceutical composition of the present invention, the pharmaceutically active ingredient can be an antiviral drug. A typical example of the antiviral drug is antihepatitis B virus drug, such as, adefovir, acyclovir, adefovir dipivoxil, entecavir, ganciclovir or the like.

Besides, in the pharmaceutical composition of the present invention, the pharmaceutically active ingredient can be other drugs than the drugs described above, for example, a polypeptide or protein drug, such as, calcitonin, interferon, insulin or the like, a polysaccharose drug, such as, heparin, hyaluronic acid, or the like.

In addition, the present invention also provides use of the PEGylated and fatty acid grafted chitosan oligosaccharide in preparation of the above-mentioned pharmaceutical composition.

EMBODIMENTS

Figure 1:
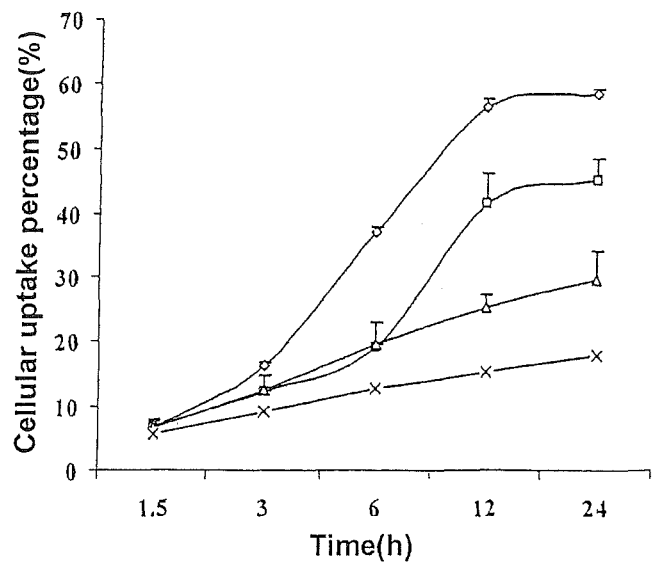
FIG. 1 shows quantitatively uptake of micelles of the PEGylated and stearic acid grafted chitosan oligosaccharide micelles in a macrophage RAW264.7. (◇): micelles of the stearic acid grafted chitosan oligosaccharide of the Comparative Example 1; (Δ): micelles of the PEGylated and stearic acid grafted chitosan oligosaccharide of the Example 2; (x): micelles of the PEGylated and stearic acid grafted chitosan oligosaccharide of the Example 3; (□): micelles of the PEGylated and stearic acid grafted chitosan oligosaccharide of the Example 1.

The present invention is described in details by means of examples below, but is in no way limited to these examples.
(1) Preparation of the PEGylated Fatty Acid Grafted Chitosan Oligosaccharide Comparative Examples 1-3

Preparation of Stearic Acid Grafted Chitosan Oligosaccharide

A chitosan (6 g, the average molecular weight: 450,000 Da) was added into an aqueous hydrochloric acid solution (200 mL, 1.25 (v/v)), and was dissolved under stirring at 55-60° C. The pH value of the resultant solution was adjusted to 5.0 with diluted ammonia or diluted hydrochloric acid. A cellulase was added in a ratio of cellulose:chitosan=0.5:100 (w/w). After a reaction for 8 h, the reaction products were centrifuged at 4000 rpm for 10 min. Subsequently, the supernatant was pretreated with a 0.45 μm microporous filter membrane, fractionated by using an ultrafiltration membrane based on different molecular weights. The ultrafiltrate was freeze-dried to give a chitosan oligosaccharide having a specific molecular weight. As measured by gel permeation chromatography, the average molecular weight of the chitosan oligosaccharide was 18,600 Da.

The above obtained chitosan oligosaccharide was weighed (5.0 g) and added into distilled water (40 mL), and was dissolved under stirring. Then, a carbodiimide (1.0 g) was added, and dissolved under stirring. In Comparative Examples 1-3, stearic acid (0.78 g, 1.5 g and 2.4 g, respectively) was added into a methanol solution (10 mL). After dissolution by ultrasonic, the resultant solution was added into the above chitosan oligosaccharide solution. Under a 400 rpm magnetic stirring and a temperature of 60° C., the reaction was conducted for more than 24 h. Subsequently, the final reaction mixture was placed into a dialysis bag, and was dialyzed with double distilled water for 24 h to remove the reaction by-products. The dialysate was freeze-dried to give a hydrophobic modified chitosan oligosaccharide, i.e., the stearic acid grafted chitosan oligosaccharide.

As measured by gel permeation chromatography wellknown in the art, the average molecular weights of stearic acid grafted chitosan oligosaccharide in Comparative Examples 1-3 were 20,000, 21,000 and 33,000 Da, respectively.

Comparative Example 4

Preparation of Lauric Acid Grafted Chitosan Oligosaccharide

A chitosan having an average molecular weight of 18,600 Da was prepared by the same method as described in the above Comparative Example 1. The above obtained chitosan oligosaccharide was weighed (5.0 g) and added into distilled water (40 mL), and was dissolved under stirring. Then, a carbodiimide (1.0 g) was added, and dissolved under stirring. A lauric acid (0.5 g) was added into a methanol solution (10 mL). After dissolution by ultrasonic, the resultant solution was added into the above chitosan oligosaccharide solution. Under a 400 rpm magnetic stirring and a temperature of 60° C., the reaction was conducted for more than 24 h. Subsequently, the final reaction mixture was placed into a dialysis bag, and was dialyzed with double distilled water for 24 h to remove the reaction by-products. The dialysate was freeze-dried to give a hydrophobic modified chitosan oligosaccharide, i.e., the lauric acid grafted chitosan oligosaccharide.

As measured by gel permeation chromatography wellknown in the art, the average molecular weights of lauric acid grafted chitosan oligosaccharide in the Comparative Example 4 were 20,000 Da.

Comparative Example 5

Preparation of Docosanoic Acid Grafted Chitosan Oligosaccharide

A chitosan having an average molecular weight of 18,600 Da was prepared by the same method as described in the above Comparative Example 1. The above obtained chitosan oligosaccharide was weighed (5.0 g) and added into distilled water (40 mL), and was dissolved under stirring. Then, a carbodiimide (1.0 g) was added, and dissolved under stirring. A docosanoic acid (1.0 g) was added into a methanol solution (10 mL). After dissolution by ultrasonic, the resultant solution was added into the above chitosan oligosaccharide solution. Under a 400 rpm magnetic stirring and a temperature of 60° C., the reaction was conducted for more than 24 h. Subsequently, the final reaction mixture was placed into a dialysis bag, and was dialyzed with double distilled water for 24 h to remove the reaction by-products. The dialysate was freeze-dried to give a hydrophobic modified chitosan oligosaccharide, i.e., the docosanoic acid grafted chitosan oligosaccharide.

As measured by gel permeation chromatography well-known in the art, the average molecular weights of docosanoic acid grafted chitosan oligosaccharide in the Comparative Example 5 were 20,500 Da.

Comparative Example 6

Preparation of Oleic Acid Grafted Chitosan Oligosaccharide

A chitosan having an average molecular weight of 18,600 Da was prepared by the same method as described in the above Comparative Example 1. The above obtained chitosan oligosaccharide was weighed (5.0 g) and added into distilled water (40 mL), and was dissolved under stirring. Then, a carbodiimide (1.0 g) was added, and dissolved under stirring. An oleic acid (0.8 g) was added into a methanol solution (10 mL). After dissolution by ultrasonic, the resultant solution was added into the above chitosan oligosaccharide solution. Under a 400 rpm magnetic stirring and a temperature of 60° C., the reaction was conducted for more than 24 h. Subsequently, the final reaction mixture was placed into a dialysis bag, and was dialyzed with double distilled water for 24 h to remove the reaction by-products. The dialysate was freeze-dried to give a hydrophobic modified chitosan oligosaccharide, i.e., the oleic acid grafted chitosan oligosaccharide.

As measured by gel permeate ion chromatography well-known in the art, the average molecular weights of oleic acid grafted chitosan oligosaccharide in the Comparative Example 6 were 20,000 Da.

Example 1

A stearic acid grafted chitosan oligosaccharide having a molecular weight of 20,000 Da (200 mg) and a terminal-aldehydated PEG having a molecular weight of 2,000 Da (2.68 mg) were weighed (the molar ratio of the terminal-aldehydated PEG to stearic acid grafted chitosan oligosaccharide was 1:5), and were dissolved in deionized water (50 mL). The resultant solution was treated with an ultrasonic probe for 20 times (at 400 w, each time working for 2 s at an interval of 3 s), and was magnetically stirred overnight (at 400 rpm) at the room temperature. Subsequently, the reaction mixture was placed into a dialysis bag (molecular weight cutoff: 7000 Da, Spectrum Laboratories, Laguna Hills, Calif.), and was dialyzed for 48 h to remove the unreacted terminal-aldehydated PEG. Then, the dialysate was freeze-dried to give a PEGylated and stearic acid grafted chitosan oligosaccharide as a solid powder.

Example 2

A PEGylated and stearic acid grafted chitosan oligosaccharide was prepared by the same method as described in the above Example 1, except that the molar ratio of the terminal-aldehydated PEG to the stearic acid grafted chitosan oligosaccharide was 1:1.

Example 3

A PEGylated and stearic acid grafted chitosan oligosaccharide was prepared by the same method as described in the above Example 1, except that the molar ratio of the terminal-aldehydated PEG to the stearic acid grafted chitosan oligosaccharide was 5:1.

Example 4

A PEGylated and stearic acid grafted chitosan oligosaccharide was prepared by the same method as described in the above Example 1, except that the molar ratio of the terminal-aldehydated PEG to the stearic acid grafted chitosan oligosaccharide was 1:10.

Example 5

A PEGylated and stearic acid grafted chitosan oligosaccharide was prepared by the same method as described in the above Example 1, except that the molar ratio of the terminal-aldehydated PEG to the stearic acid grafted chitosan oligosaccharide was 1:20.

Example 6

A PEGylated and stearic acid grafted chitosan oligosaccharide was prepared by the same method as described in the above Example 1, except that the molar ratio of the terminal-aldehydated PEG to the stearic acid grafted chitosan oligosaccharide was 80:1.

Example 7

A stearic acid grafted chitosan oligosaccharide having a molecular weight of 21,000 Da (200 mg) and a terminal-aldehydated PEG having a molecular weight of 2,000 Da (380 mg) were weighed (the molar ratio of the terminal-aldehydated PEG to stearic acid grafted chitosan oligosaccharide was 20:1), and were dissolved in deionized water (50 mL). The resultant solution was treated with an ultrasonic probe for 20 times (at 400 w, each time working for 2 s at an interval of 3 s), and was magnetically stirred overnight (at 400 rpm) at the room temperature. Subsequently, the reaction mixture was placed into a dialysis bag (molecular weight cutoff: 7000 Da, Spectrum Laboratories, Laguna Hills, Calif.), and was dialyzed for 48 h to remove the unreacted terminal-aldehydated PEG Then, the dialysate was freeze-dried to give a PEGylated and stearic acid grafted chitosan oligosaccharide as a solid powder.

Example 8

A stearic acid grafted chitosan oligosaccharide having a molecular weight of 33,000 Da (200 mg) and a terminal-aldehydated PEG having a molecular weight of 2,000 Da (363 mg) were weighed (the molar ratio of the terminal-aldehydated PEG to stearic acid grafted chitosan oligosaccharide was 30:1), and were dissolved in deionized water (50 mL). The resultant solution was treated with an ultrasonic probe for 20 times (at 400 w, each time working for 2 s at an interval of 3 s), and was magnetically stirred overnight (at 400 rpm) at the room temperature. Subsequently, the reaction mixture was placed into a dialysis bag (molecular weight cutoff: 7000 Da, Spectrum Laboratories, Laguna Hills, Calif.), and was dialyzed for 48 h to remove the unreacted terminal-aldehydated PEG Then, the dialysate was freeze-dried to give a PEGylated and stearic acid grafted chitosan oligosaccharide as a solid powder.

Example 9

A PEGylated and stearic acid grafted chitosan oligosaccharide was prepared by the same method as described in the above Example 1, except that the terminal-aldehydated PEG has a molecular weight of 1,000 Da, and the molar ratio of the terminal-aldehydated PEG to the stearic acid grafted chitosan oligosaccharide was 20:1.

Example 10

A PEGylated and stearic acid grafted chitosan oligosaccharide was prepared by the same method as described in the above Example 1, except that the terminal-aldehydated PEG has a molecular weight of 10,000 Da, and the molar ratio of the terminal-aldehydated PEG to the stearic acid grafted chitosan oligosaccharide was 2:1.

Example 11

A stearic acid grafted chitosan oligosaccharide having a molecular weight of 20,000 Da (100 mg), a terminal-carboxylated PEG having a molecular weight of 2,000 Da (100 mg) and a carbodiimide (100 mg) were weighed (the molar ratio of the terminal-carboxylated PEG to stearic acid grafted chitosan oligosaccharide was 10:1), and were dissolved in deionized water (50 mL). The resultant solution was treated with an ultrasonic probe for 20 times (at 400 w, each time working for 2 s at an interval of 3 s), and was magnetically stirred (at 400 rpm) at a temperature of 60° C. for 48 h. Subsequently, the reaction mixture was placed into a dialysis bag (molecular weight cutoff: 7000 Da, Spectrum Laboratories, Laguna Hills, Calif.), and was dialyzed for 48 h to remove the unreacted terminal-carboxylated PEG. Then, the dialysate was freeze-dried to give a PEGylated and stearic acid grafted chitosan oligosaccharide as a solid powder.

Example 12

A stearic acid grafted chitosan oligosaccharide having a molecular weight of 20,000 Da (100 mg) and a terminal-succinimidated PEG having a molecular weight of 2,000 Da (100 mg) were weighed (the molar ratio of the terminal-succinimidated PEG to stearic acid grafted chitosan oligosaccharide was 10:1), and were dissolved in deionized water (50 mL). The resultant solution was treated with an ultrasonic probe for 20 times (at 400 w, each time working for 2 s at an interval of 3 s), and was magnetically stirred (at 400 rpm) at the room temperature for 48 h. Subsequently, the reaction mixture was placed into a dialysis bag (molecular weight cutoff: 7000 Da, Spectrum Laboratories, Laguna Hills, Calif.), and was dialyzed for 48 h to remove the unreacted terminal-succinimidated PEG. Then, the dialysate was freeze-dried to give a PEGylated and stearic acid grafted chitosan oligosaccharide as a solid powder.

Example 13

A stearic acid grafted chitosan oligosaccharide having a molecular weight of 20,000 Da (100 mg) and a terminal-maleic anhydridated PEG having a molecular weight of 2,000 Da (100 mg) were weighed (the molar ratio of the terminal-maleic anhydridated PEG to stearic acid grafted chitosan oligosaccharide was 10:1), and were dissolved in deionized water (50 mL). The resultant solution was treated with an ultrasonic probe for 20 times (at 400 w, each time working for 2 s at an interval of 3 s), and was magnetically stirred (at 400 rpm) at the room temperature for 48 h. Subsequently, the reaction mixture was placed into a dialysis bag (molecular weight cutoff: 7000 Da, Spectrum Laboratories, Laguna Hills, Calif.), and was dialyzed for 48 h to remove the unreacted terminal-maleic anhydridated PEG. Then, the dialysate was freeze-dried to give a PEGylated and stearic acid grafted chitosan oligosaccharide as a solid powder.

Example 14

A lauric acid grafted chitosan oligosaccharide having a molecular weight of 20,000 Da obtained in the Comparative Example 4 (200 mg) and a terminal-aldehydated PEG having a molecular weight of 2,000 Da (200 mg) were weighed (the molar ratio of the terminal-aldehydated PEG to lauric acid grafted chitosan oligosaccharide was 10:1), and were dissolved in deionized water (50 mL). The resultant solution was treated with an ultrasonic probe for 20 times (at 400 w, each time working for 2 s at an interval of 3 s), and was magnetically stirred overnight (at 400 rpm) at the room temperature. Subsequently, the reaction mixture was placed into a dialysis bag (molecular weight cutoff: 7000 Da, Spectrum Laboratories, Laguna Hills, Calif.), and was dialyzed for 48 h to remove the unreacted terminal-aldehydated PEG. Then, the dialysate was freeze-dried to give a PEGylated and lauric acid grafted chitosan oligosaccharide as a solid powder.

Example 15

A docosanoic acid grafted chitosan oligosaccharide having a molecular weight of 20,500 Da obtained in the Comparative Example 5 (200 mg) and a terminal-aldehydated PEG having a molecular weight of 2,000 Da (194 mg) were weighed (the molar ratio of the terminal-aldehydated PEG to docosanoic acid grafted chitosan oligosaccharide was 10:1), and were dissolved in deionized water (50 mL). The resultant solution was treated with an ultrasonic probe for 20 times (at 400 w, each time working for 2 s at an interval of 3 s), and was magnetically stirred overnight (at 400 rpm) at the room temperature. Subsequently, the reaction mixture was placed into a dialysis bag (molecular weight cutoff: 7000 Da, Spectrum Laboratories, Laguna Hills, Calif.), and was dialyzed for 48 h to remove the unreacted terminal-aldehydated PEG. Then, the dialysate was freeze-dried to give a PEGylated docosanoic acid grafted chitosan oligosaccharide as a solid powder.

Example 16

A oleic acid grafted chitosan oligosaccharide having a molecular weight of 20,000 Da obtained in the Comparative Example 6 (200 mg) and a terminal-aldehydated PEG having a molecular weight of 2,000 Da (200 mg) were weighed (the molar ratio of the terminal-aldehydated PEG to oleic acid grafted chitosan oligosaccharide was 10:1), and were dissolved in deionized water (50 mL). The resultant solution was treated with an ultrasonic probe for 20 times (at 400 w, each time working for 2 s at an interval of 3 s), and was magnetically stirred overnight (at 400 rpm) at the room temperature. Subsequently, the reaction mixture was placed into a dialysis bag (molecular weight cutoff: 7000 Da, Spectrum Laboratories, Laguna Hills, Calif.), and was dialyzed for 48 h to remove the unreacted terminal-aldehydated PEG. Then, the dialysate was freeze-dried to give a PEGylated oleic acid grafted chitosan oligosaccharide as a solid powder.

(2) Properties of the PEGylated Fatty Acid Grafted Chitosan Oligosaccharide

The fatty acid grafted chitosan oligosaccharide obtained in the above Comparative Examples 1-6 (10 mg) and the PEGylated fatty acid grafted chitosan oligosaccharide (10 mg) obtained in the above Examples 1-16 were respectively weighed, and were dispersed in appropriate amount of double distilled water by an ultrasound in water bath for 10 min. Then, the volume was set to 100 mL to give the corresponding micellar solution. A Zetasizer 3000HS analyzer was used to measure the average particle diameter (D) and surface potential (Zeta) of micelles in the solution. The critical micelle concentrations (CMC) of the unmodified or PEGylated and fatty acid grafted chitosan oligosaccharide in PBS were measured, respectively, by the pyrene fluorescence method well-know in the art. The grafting ratios of PEG and fatty acids in the PEGylated and fatty acid grafted chitosan oligosaccharide were measured by the trinitrobenzene-sulfonic acid (TNBS) method well-known in the art, and then the substitution degree of amino groups can be obtained. The above properties of the Example 1-16 and Comparative Examples 1-6 were shown in the following Table 1.

TABLE 1

|  | D (nm) | Zeta (mV) | CMC (μg/mL) | Grafting ratio of PEG (%) | Grafting ratio of fatty acid (%) | Substitution degree of amino (%) |
|---|---|---|---|---|---|---|
| Comparative Example 1 | 103.4 | 20.1 | 13.8 | 0 | 5 | 5 |
| Comparative Example 2 | 98.6 | 25.2 | 11.4 | 0 | 8 | 8 |
| Comparative Example 3 | 45.2 | 24.3 | 8.6 | 0 | 48.3 | 48.3 |
| Comparative Example 4 | 124.3 | 23.8 | 15.7 | 0 | 7 | 7 |
| Comparative Example 5 | 66.8 | 34.6 | 8.8 | 0 | 4 | 4 |
| Comparative Example 6 | 88.2 | 26.7 | 12.9 | 0 | 5 | 5 |
| Example 1 | 119.2 | 14.1 | 12.5 | 0.1 | 5 | 5.1 |
| Example 2 | 161.2 | 14.3 | 11.5 | 1 | 5 | 6 |
| Example 3 | 171.8 | 15.9 | 11.7 | 4 | 5 | 9 |
| Example 4 | 178.2 | 15.5 | 12.9 | 0.1 | 5 | 5.1 |
| Example 5 | 185.2 | 16.1 | 13.5 | 0.05 | 5 | 5.05 |
| Example 6 | 85.2 | 22.5 | 42.6 | 50 | 5 | 55 |
| Example 7 | 96.3 | 32.5 | 25.6 | 8.1 | 8 | 16.1 |
| Example 8 | 74.3 | 35.5 | 12.4 | 8.1 | 48.3 | 56.4 |
| Example 9 | 105.4 | 34.2 | 31.7 | 15 | 5 | 20 |
| Example 10 | 196.5 | 38.7 | 47.8 | 1.6 | 5 | 6.6 |
| Example 11 | 87.3 | 35.5 | 55.2 | 7.6 | 5 | 12.6 |
| Example 12 | 76.8 | 33.8 | 49.7 | 8.1 | 5 | 13.1 |
| Example 13 | 79.1 | 37.2 | 50.1 | 8.3 | 5 | 13.3 |
| Example 14 | 146.3 | 32.7 | 43.2 | 7.8 | 7 | 14.8 |
| Example 15 | 78.2 | 38.2 | 38.9 | 8.6 | 4 | 12.6 |
| Example 16 | 98.4 | 32.6 | 145.7 | 8.3 | 5 | 13.3 |

It can be seen that the PEGylated and fatty acid grafted chitosan oligosaccharide of the present invention has a property to form micelles by self-assembly in an aqueous media. Further, the PEGylated and fatty acid grafted chitosan oligosaccharide of the present invention has a CMC significantly lower than that of common surfactants. The micelle formed of the PEGylated and fatty acid grafted chitosan oligosaccharide of the present invention as a drug delivery system has many advantages. It can control in vivo release of a pharmaceutically active ingredient by regulating properties of the material, such as, grafting ratios of PEG and fatty acids, solubility, pH value, zeta potential and the like. Since the particle size of the micelle is rather small, it can not only permeate through blood-brain barrier and reticuloendothelial system, but also promote absorption of gastrointestinal mucosa and the like, so as to reach the location where large-size particles can not pass through, thereby achieving a purpose of a passive targeting. A protection and shielding effect of the polymer micelle skeleton can prevent the drug from being decomposed to some extent, maintain stability of the drug and reduce toxicity of the drug. In comparison to liposomes, drug loading of the polymer micelle is relatively higher. Diversity in the structure of PEG-modified chitosan oligosaccharide fatty acid graft is in favor of production of diversified pharmaceutical preparations using the polymer as a carrier, thereby meeting requirements of various applications. Therefore, the PEGylated and fatty acid grafted chitosan oligosaccharide of the present invention can be applied in preparation of numerous pharmaceutical compositions as a carrier.

(3) The Uptake of PEGylated Fatty Acid Grafted Chitosan Oligosaccharide Micelles in Different Cell Lines 10 mg stearic acid grafted chitosan oligosaccharide of comparative example 1 and PEGylated and stearic acid grafted chitosan oligosaccharide of embodiments 1-3 were respectively weighed, dissolved in 2 mL deionized water, and treated with ultrasonic probe for 20 times (400 w, stimulation time 2 s and intermission time 3 s); and then, 200 μL ethanol solution containing 2.0 mg/mL fluorescein isothiocyanate, (FITC) was added, prior to continuous reaction for 24 h under the condition of magnetic stirring (400 rpm) in dark. Subsequently, the final reaction mixture was dialyzed in dialysis bag (with the molecular weight cutoff of 7000 Da, Spectrum Laboratories, Laguna Hills, Calif.) for 24 h with deionized water to remove unreacted FITC. After the dialysate was freeze-dried, the fluorescence labeled product of PEGylated and stearic acid grafted chitosan oligosaccharide was obtained.

RAW264.7 cell (macrophage), HepG2 cell (hepatoma cell) and BRL-3A cell (immortalized normal liver cell) were continuously cultured in DMEM supplemented with 10% fetal bovine serum (RAW264.7 and HepG2) and 1640 medium supplemented with 10% new-born calf serum (BRL-3A) in 5% $CO_2$, 37° C. incubator till logarithmic growth phase. And then, after trypsin digestion, the cells were diluted with culture medium, inoculated to 24-well culture plates (Nalge Nune International, Naperville, Ill., USA) with the inoculum density of $1\times10^5$ per well and cultured in incubator for 24 h. Then, the FITC labeled PEGylated and stearic acid grafted chitosan oligosaccharide micellar solution was added to the culture medium for incubation, with the added concentration of micelle was controlled at 100 μg/ml. After the cells were cultured for 1.5, 3, 6, 12 and 24 h respectively, they were washed with PBS and digested by trypsin. The cell digestion solution was harvested and treated with ultrasonic probe for 20 times (400 w, stimulation time 2 s and intermission time 3 s) to obtain cell lysate. The fluorescence spectrophotometer was used to determine the fluorescence intensity of the cell lysate, and then the uptake percentage of PEGylated and stearic acid grafted chitosan oligosaccharide in cells was calculated and corrected with protein. The uptake percentage of micelle in cells was calculated according to the following formula:

$$P_t(\%) = F_t/F_0 \times 100\%$$

Wherein, $P_t$ refers to the uptake percentage of micelle in cells during t time period; $F_t$ and $F_0$ respectively represent the fluorescence absorption (which has been corrected with protein) at t time and 0 time.

Figure 2:
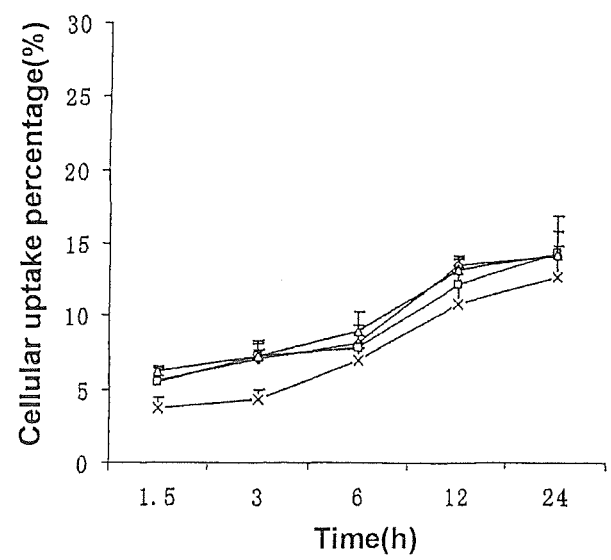
FIG. 2 shows quantitatively uptake of micelles of the PEGylated and stearic acid grafted chitosan oligosaccharide micelles in the hepatoma cell HepG2. (◇): micelles of the stearic acid grafted chitosan oligosaccharide of the Comparative the Example 1; (Δ): micelles of the PEGylated and stearic acid grafted chitosan oligosaccharide of the Example 2; (x): micelles of the PEGylated and stearic acid grafted chitosan oligosaccharide of the Example 3; (□): micelles of the PEGylated and stearic acid grafted chitosan oligosaccharide of the Example 1.
Figure 3:
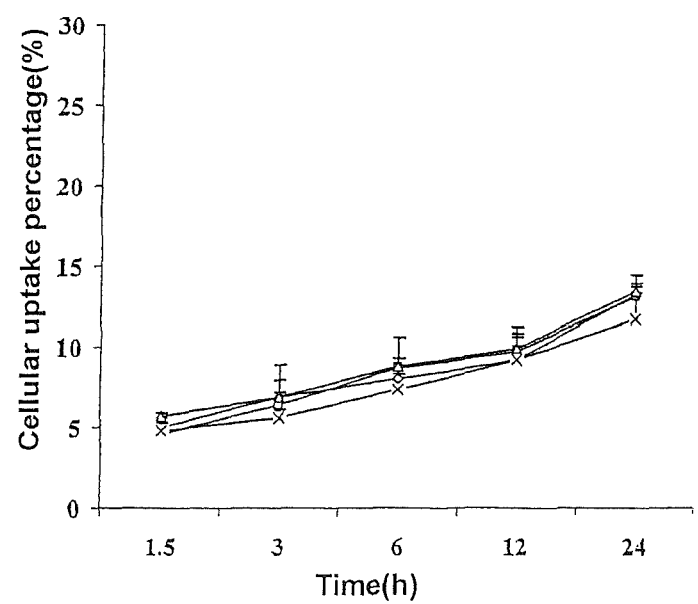
FIG. 3 shows quantitatively uptake of micelles of the PEGylated and stearic acid grafted chitosan oligosaccharide micelles in the immortalized normal liver cell BRL-3A. (◇): micelles of the stearic acid grafted chitosan oligosaccharide of the Comparative Example 1; (Δ): micelles of the PEGylated and stearic acid grafted chitosan oligosaccharide of the Example 2; (x): micelles of the PEGylated and stearic acid grafted chitosan oligosaccharide of the Example 3; (□): micelles of the PEGylated and stearic acid grafted chitosan oligosaccharide of the Example 1.

The uptake results of stearic acid grafted chitosan oligosaccharide of comparative example 1 and PEGylated and stearic acid grafted chitosan oligosaccharide of embodiments 1-3 by RAW264.7 cell, HepG2 cell and BRL-3A cell were shown in FIGS. 1-3. In addition, the uptake results of above micelles in RAW264.7 cells, HepG2 cells and BRL-3A cells within 24 h were listed in Table 2.

TABLE 2

| | Grafting ratio of PEG (%) | Uptake percentage within 24 h (%) | | |
|---|---|---|---|---|
| | | RAW264.7 | HepG2 | BRL-3A |
| Comparative example 1 | 0 | 58.4 ± 0.63 | 14.1 ± 1.7 | 13.2 ± 0.5 |
| Embodiment 1 | 0.1 | 45.0 ± 3.25 | 14.3 ± 2.6 | 13.1 ± 1.2 |
| Embodiment 2 | 1 | 29.6 ± 4.5 | 14.2 ± 1.6 | 13.4 ± 0.5 |
| Embodiment 3 | 4 | 17.7 ± 17.1 | 12.6 ± 2.2 | 11.7 ± 1.5 |

It could be concluded from the above results that, compared with the unmodified stearic acid grafted chitosan oligosaccharide micelle (comparative example 1), the uptake amount of PEGylated and stearic acid grafted chitosan oligosaccharide (embodiments 1-3) in macrophage RAW264.7 cell within the same time period was significantly reduced. Besides, with the increase of proportion of PEG modification (grafting ratio of PEG), the uptake amount of the micelles in macrophages was gradually decreased.

In addition, the uptake amounts of PEGylated and stearic acid grafted chitosan oligosaccharide (embodiments 1-3) in tumor cell HepG2 and normal cell BRL-3A within the same time period had no significant difference compared with that of unmodified stearic acid grafted chitosan oligosaccharide micelle (comparative example 1).

Accordingly, it can be expected that PEGylated and stearic acid grafted chitosan oligosaccharide can greatly reduce the possibility that the carrier is phagocytized by the macrophages in blood, and thus increase the cycle time of the carrier material in organism and the distribution of carrier material in target tissues. Meanwhile, PEGylation does not affect the uptake of carrier material in tumor cells. Therefore, the targeting delivery of drugs in tumor cells can be increased by using the carrier material.

(4) Application of PEGylated and Fatty Acid Grafted Chitosan Oligosaccharide Micelle in Anticancer Drug Composition (4.1) Application of PEGylated Stearic Acid Grafted Chitosan Oligosaccharide (a) Mitomycin C Preparation 10 mg stearic acid grafted chitosan oligosaccharide of comparative example 1 and PEGylated and stearic acid grafted chitosan oligosaccharide of embodiments 1-3 were respectively weighed and dissolved in 1.5 mL PBS. After 0.5 mL of 1 mg/mL mitomycin C PBS solution was added, the solution was treated with ultrasonic probe for 20 times (400 w, stimulation time 2 s and intermission time 3 s) to obtain the mitomycin C-loaded PEGylated and stearic acid grafted chitosan oligosaccharide micelle solution, of which, the material concentration was 5 mg/mL, the drug encapsulation efficiency was 30%.

By using hepatoma cell HepG2 as the model, the anticancer efficacy of mitomycin C-loaded PEGylated and stearic acid grafted chitosan oligosaccharide micelle was evaluated by the 50% inhibiting concentration ($IC_{50}$) after the drug delivery system was co-incubated with cells. Cell survival rate was determined by MTT assay. After the adherent cells were precultured in 24-well plates for 24 h, different concentrations of mitomycin C solution (the dissolvent was PBS) and mitomycin C-loaded PEGylated and stearic acid grafted chitosan oligosaccharide micelle were respectively added, and the control wells were set, with 3 repetitions of each group. After incubation for 48 h, 60 μL of MTT solution was added to each well followed by incubation for 4 h. After that, the supernatant was discarded, and the cells were washed twice with PBS solution, prior to adding 400 μL DMSO to each well to terminate the reaction. After the culture plates were given a horizontal vibration for 10 min, the absorbance at the wavelength of 570 nm was measured in ELSA meter, and the cell survival rate was calculated according to the following formula:

$$\text{Cell survival rate}(\%) = A_{570}(\text{sample})/A_{570}(\text{control}) \times 100\%$$

Wherein, $A_{570}$ (sample) is the absorbance of cells adding with free drug or drug-loaded micelle, $A_{570}$ (control) is the absorbance of control cells.

In addition, the same method was used to determine the $IC_{50}$ value of mitomycin C solution used as the control example.

The results of above tests are shown in Table 3.

TABLE 3

| | Control example | Comparative example 1 | Embodiment 1 | Embodiment 2 | Embodiment 3 |
|---|---|---|---|---|---|
| $IC_{50}$ (μg/mL) | 1.97 | 0.13 | 0.12 | 0.14 | 0.11 |

It could be concluded from the above results that, compared with that of mitomycin C solution (control example), the drug efficacy of the mitomycin C-loaded PEGylated and stearic acid grafted chitosan oligosaccharide micelle (embodiments 1-3) in the invention was increased by about 14 times. Besides, the drug efficacy of mitomycin C-loaded PEGylated and stearic acid grafted chitosan oligosaccharide (embodiments 1-3) corresponded with that of mitomycin C-loaded stearic acid grafted chitosan oligosaccharide micelle (comparative example 1). Thus, PEGylation does not affect the anti-tumor activity of drug-loaded micelles.

(b) Adriamycin Preparation 50 mg PEGylated and stearic acid grafted chitosan oligosaccharide prepared in embodiment 7 (the molecular weight of PEG is 2,000 Da; the molecular weight of chitosan oligosaccharide is 18,600 Da; the grafting ratio of PEG was 8.1%; the grafting ratio of stearic acid was 8%) was weighed and placed in 50 mL beaker, and then treated with ultrasonic probe for 20 times (500 w, stimulation time 2 s and intermission time 3 s) by adding 40 mL of distilled water (pH 5.7). Subsequently, the solution was transferred into a volumetric flask to set the total volume to 50 mL with distilled water, and then 1 mg/mL micelle solution was obtained. 20 mL of the PEGylated and stearic acid grafted chitosan oligosaccharide micelle solution was taken and added with 2 mL dimethyl sulfoxide solution containing 1 mg/mL adriamycin. After stirred at room temperature for 3 h, the solution was dialyzed for 24 h with distilled water in dialysis bag with the molecular weight of 3,500. Then the dialysis concentrate solution was centrifuged at 5000 rpm for 5 min to remove the dialyzed hydrophobic anticancer drugs. After the supernatant was filtered with 0.22 μm microporous membrane, the adriamycin-loaded PEGylated and stearic acid grafted chitosan oligosaccharide micelle was obtained.

By determination, the particle diameter of PEGylated and stearic acid grafted chitosan oligosaccharide micelle was 55.8 nm and the surface potential was 31.7 mV. Drug encapsulation efficiency was 97.2%.

Subsequently, the evaluation of antitumor efficacy was conducted. Specifically, the uterine cervix cancer cell Hela used as the model was cultured in 96-well culture plate. 100 μL cell culture solution containing $5 \times 10^3$ Hela cells was added to each well and cultured for 24 h in 37° C., 5% $CO_2$ incubator. After the cells completely adhered to the plate, different concentrations of PEGylated and stearic acid grafted chitosan oligosaccharide, drug-loaded PEGylated and stearic acid grafted chitosan oligosaccharide micelle solution and doxorubicin hydrochloride solution were respectively added to the wells, and the untreated blank cells were used as control. A repeated well of each above group was set. The cells were cultured in normal DMEM medium for 48. After 20 μL of 5 mg/mL methylthiazoletetrazolium (MTT) solution was added to each well, the cells was re-cultured in 37° C., 5% $CO_2$ incubator for 4 h, and then the supernatant was discarded. By adding 150 μL dimethyl sulfoxide to each well, a multi-functional microplate reader was used to measure the absorbance, and then the cell inhibition ratio was calculated according to the following formula:

Cell inhibition ratio(%)=(absorbance of control group−absorbance of experimental group)/absorbance of control group×100%

By calculation, the $IC_{50}$ value of PEGylated and stearic acid grafted chitosan oligosaccharide was 563.5 μg/mL; the $IC_{50}$ value of adriamycin solution was 1.7 μg/mL; and the $IC_{50}$ value of drug-loaded PEGylated and stearic acid grafted chitosan oligosaccharide micelle solution was 0.2 μg/mL. The results suggested that PEGylated and stearic acid grafted chitosan oligosaccharide was low toxicity material, and after adriamycin was encapsulated by PEGylated and stearic acid grafted chitosan oligosaccharide, its anti-tumor efficacy to uterine cervix cancer cell Hela could be increased by 8.5 times.

(c) Paclitaxel Preparation 50 mg PEGylated and stearic acid grafted chitosan oligosaccharide prepared in embodiment 8 (the molecular weight of PEG is 2,000 Da; the molecular weight of chitosan oligosaccharide is 18,600 Da; the grafting ratio of PEG was 8.1%; the grafting ratio of stearic acid was 48.3%) was weighed and placed in 50 mL beaker, and then treated with ultrasonic probe for 20 times (500 w, stimulation time 2 s and intermission time 3 s) by adding 40 mL distilled water (pH 5.7).

Subsequently, the solution was transferred into a volumetric flask to set the total volume to 50 mL with distilled water, and then 1 mg/mL micelle solution was obtained. 20 mL of the PEGylated and stearic acid grafted chitosan oligosaccharide micelle solution was taken and added with 2 mL dimethyl sulfoxide containing 1 mg/mL paclitaxel. After stirred at room temperature for 3 h, the solution was dialyzed for 24 h with distilled water in dialysis bag with the molecular weight of 3,500. Then the dialysis concentrate solution was centrifuged at 5000 rpm for 5 min to remove the dialyzed hydrophobic anticancer drugs. After the supernatant was filtered with 0.22 μm microporous membrane, the paclitaxel-loaded PEGylated and stearic acid grafted chitosan oligosaccharide micelle was obtained.

By determination, the particle diameter of drug-loaded PEGylated and stearic acid grafted chitosan oligosaccharide micelle was 89.1 nm and the surface potential was 28.7 mV. Drug encapsulation efficiency was 99.6%.

Subsequently, the antitumor efficacy of PEGylated and stearic acid grafted chitosan oligosaccharide was evaluated by inhibition ratio of tumor cells. Specifically, the human lung cancer cell A549 used as the model was cultured in 96-well culture plate. 100 μL cell culture solution containing 5×10³ A549 cells was added to each well and cultured for 24 h in 37° C., 5% $CO_2$ incubator. After the cells completely adhered to the plate, different concentrations of PEGylated and stearic acid grafted chitosan oligosaccharide, drug-loaded PEGylated and stearic acid grafted chitosan oligosaccharide micelle solution and taxol solution were respectively added to the wells, and the untreated blank cells were used as control. A repeated well of each above group was set. The cells were cultured in normal DMEM medium for 48. After 20 μL of 5 mg/mL methylthiazoletetrazolium (MTT) solution was added to each well, the cells was re-cultured in 37° C., 5% $CO_2$ incubator for 4 h, and then the supernatant was discarded. By adding 150 μL dimethyl sulfoxide to each well, a multi-functional microplate reader was used to measure the absorbance, and then the cell inhibition ratio was calculated according to the following formula:

Cell inhibition ratio %=(absorbance of control group−absorbance of experimental group)/absorbance of control group×100%

By calculation, the $IC_{50}$ value of PEGylated and stearic acid grafted chitosan oligosaccharide was 489.6 μg/mL; the $IC_{50}$ value of taxol solution was 3.2 μg/mL; and the $IC_{50}$ value of drug-loaded PEGylated and stearic acid grafted chitosan oligosaccharide micelle solution was 0.1 μg/mL. The results suggested that PEGylated and stearic acid grafted chitosan oligosaccharide was low toxicity material, and after paclitaxel was encapsulated by PEGylated and stearic acid grafted chitosan oligosaccharide, its anti-tumor efficacy to human lung cancer cell A549 could be increased by 32 times.

(d) Hydroxycamptothecin Preparation 50 mg PEGylated and stearic acid grafted chitosan oligosaccharide prepared in embodiment 7 (the molecular weight of PEG is 2,000 Da; the molecular weight of chitosan oligosaccharide is 18,600 Da; the grafting ratio of PEG was 8.1%; the grafting ratio of stearic acid was 8%) was weighed and placed in 50 mL beaker, and then treated with ultrasonic probe for 20 times (500 w, stimulation time 2 s and intermission time 3 s) by adding 40 mL distilled water (pH 5.7). Subsequently, the solution was transferred into a volumetric flask to set the total volume to 50 mL with distilled water, and then 1 mg/mL micelle solution was obtained. 20 mL of the PEGylated and stearic acid grafted chitosan oligosaccharide micelle solution was taken and added with 2 mL ethanol containing 1 mg/mL hydroxycamptothecin. After stirred at room temperature for 3 h, the solution was dialyzed for 24 h with distilled water in dialysis bag with the molecular weight of 3,500 Da. The dialysis concentrate solution was centrifuged at 5000 rpm for 5 min to remove the dialyzed hydrophobic anticancer drugs. After the supernatant was filtered with 0.22 μm microporous membrane, the hydroxycamptothecin-loaded PEGylated and stearic acid grafted chitosan oligosaccharide micelle was obtained.

By determination, the particle diameter of drug-loaded PEGylated and stearic acid grafted chitosan oligosaccharide micelle was 72.9 nm and the surface potential was 36.2 mV. Drug encapsulation efficiency was 89.4%.

Subsequently, the antitumor efficacy of PEGylated and stearic acid grafted chitosan oligosaccharide was evaluated by inhibition ratio of tumor cells. Specifically, the human lung cancer cell A549 used as the model was cultured in 96-well culture plate. 100 μL cell culture solution containing 5×10³ A549 cells was added to each well and cultured for 24 h in 37° C., 5% $CO_2$ incubator. After the cells completely adhered to the plate, different concentrations of PEGylated and stearic acid grafted chitosan oligosaccharide, drug-loaded PEGylated and stearic acid grafted chitosan oligosaccharide micelle solution and hydeoxycamptothecin injection were respectively added to the wells, and the untreated blank cells were used as control. A repeated well of each above group was set. The cells were cultured in normal DMEM medium for 48. After 20 μL of 5 mg/mL methylthiazoletetrazolium (MTT) solution was added to each well, the cells was re-cultured in 37° C., 5% CO$_2$ incubator for 4 h, and then the supernatant was discarded. By adding 150 μL dimethyl sulfoxide to each well, a multi-functional microplate reader was used to measure the absorbance, and then the cell inhibition ratio was calculated according to the following formula:

Cell inhibition ratio %=(absorbance of control group–absorbance of experimental group)/absorbance of control group×100%

By calculation, the IC$_{50}$ value of PEGylated and stearic acid grafted chitosan oligosaccharide was 496.3 μg/mL; the IC$_{50}$ value of hydeoxycamptothecin injection was 8.6 μg/mL; and the IC$_{50}$ value of drug-loaded PEGylated and stearic acid grafted chitosan oligosaccharide micelle solution was 0.4 μg/mL. The results suggested that PEGylated and stearic acid grafted chitosan oligosaccharide was low toxicity material, and after hydroxycamptothecin was encapsulated by PEGylated and stearic acid grafted chitosan oligosaccharide, its anti-tumor efficacy to human lung cancer cell A549 could be increased by 21.5 times.

(4.2) Application of PEGylated and Lauric Acid Grafted Chitosan Oligosaccharide 50 mg PEGylated and lauric acid grafted chitosan oligosaccharide prepared in embodiment 14 was taken to prepare drug-loaded PEGylated and lauric acid grafted chitosan oligosaccharide micelle by using the same method in above (4.1) (c).

By determination, the particle diameter of PEGylated and lauric acid grafted chitosan oligosaccharide micelle was 123.7 nm and the surface potential was 31.4 mV. Drug encapsulation efficiency was 99.3%.

Subsequently, the antitumor efficacy of PEGylated and lauric acid grafted chitosan oligosaccharide was evaluated by using the same method in the above (4.1) (c). Evaluation results show that the IC$_{50}$ value of PEGylated and lauric acid grafted chitosan oligosaccharide was 456.1 μg/mL; the IC$_{50}$ value of taxol solution was 3.2 μg/mL; and the IC$_{50}$ value of drug-loaded PEGylated and lauric acid grafted chitosan oligosaccharide micelle solution was 0.1 μg/mL. The results suggested that PEGylated and lauric acid grafted chitosan oligosaccharide was low toxicity material, and after paclitaxel was encapsulated by PEGylated and lauric acid grafted chitosan oligosaccharide, its anti-tumor efficacy to human lung cancer cell A549 could be increased by 32 times.

(4.3) Application of PEGylated and Docosanoic Acid Grafted Chitosan Oligosaccharide 50 mg PEGylated and docosanoic acid grafted chitosan oligosaccharide prepared in embodiment 15 was taken to prepare drug-loaded PEGylated and docosanoic acid grafted chitosan oligosaccharide micelle by using the same method in above (4.1) (c).

By determination, the particle diameter of PEGylated and docosanoic acid grafted chitosan oligosaccharide micelle was 86.4 nm and the surface potential was 33.1 mV. Drug encapsulation efficiency was 99.8%.

Subsequently, the antitumor efficacy of drug-loaded PEGylated and docosanoic acid grafted chitosan oligosaccharide was evaluated by using the same method in the above (4.1) (c). Evaluation results show that the IC$_{50}$ value of PEGylated and docosanoic acid grafted chitosan oligosaccharide was 438.8 μg/mL; the IC$_{50}$ value of taxol solution was 3.2 μg/mL; and the IC$_{50}$ value of drug-loaded PEGylated and docosanoic acid grafted chitosan oligosaccharide micelle solution was 0.2 μg/mL. The results suggested that PEGylated and docosanoic acid grafted chitosan oligosaccharide was low toxicity material, and after paclitaxel was encapsulated by PEGylated and docosanoic acid grafted chitosan oligosaccharide, its anti-tumor efficacy to human lung cancer cell A549 could be increased by 16 times.

(4.4) Application of PEGylated and Oleic Acid Grafted Chitosan Oligosaccharide 50 mg PEGylated and oleic acid grafted chitosan oligosaccharide prepared in embodiment 16 was taken to prepare drug-loaded PEGylated and oleic acid grafted chitosan oligosaccharide micelle by using the same method in above (4.1) (c).

By determination, the particle diameter of drug-loaded PEGylated and oleic acid grafted chitosan oligosaccharide micelle was 109.2 nm and the surface potential was 35.2 mV. Drug encapsulation efficiency was 99.4%.

Subsequently, the antitumor efficacy of drug-loaded PEGylated and oleic acid grafted chitosan oligosaccharide was evaluated by using the same method in the above (4.1) (c). Evaluation results show that the IC$_{50}$ value of PEGylated and oleic acid grafted chitosan oligosaccharide was 413.7 μg/mL; the IC$_{50}$ value of taxol solution was 3.2 μg/mL; and the IC$_{50}$ value of drug-loaded PEGylated and oleic acid grafted chitosan oligosaccharide micelle solution was 0.1 μg/mL. The results suggested that PEGylated and oleic acid grafted chitosan oligosaccharide was low toxicity material, and after paclitaxel was encapsulated by PEGylated and oleic acid grafted chitosan oligosaccharide, its anti-tumor efficacy to human lung cancer cell A549 could be increased by 32 times.

(5) Application of PEGylated and Fatty Acid Grafted Chitosan Oligosaccharide in the Reversal of Drug Resistance of Tumor (a) Adriamycin Preparation The same method in the above (4.1) (b) was used to prepare adriamycin-loaded PEGylated and stearic acid grafted chitosan oligosaccharide micelle.

By determination, the particle diameter of PEGylated and stearic acid grafted chitosan oligosaccharide micelle was 67.2 nm and the surface potential was 38.3 mV. Drug encapsulation efficiency was 96.4%.

Subsequently, the inhibition ratio of tumor cells was used to evaluate the antitumor efficacy of drug-loaded PEGylated and stearic acid grafted chitosan oligosaccharide and the reversal efficiency of drug resistance of drug-resistant tumor cells.

Specifically, the breast carcinoma cell (MCF-7) and its drug-resistant cell (MCF-7-adr) used as the model cells were cultured in 96-well culture plate. 100 μL culture solution containing 5×10$^3$ MCF-7 or MCF-7-adr cells was added to each well and cultured for 24 h in 37° C., 5% CO$_2$ incubator. After the cells completely adhered to the plate, different concentrations of PEGylated and stearic acid grafted chitosan oligosaccharide, drug-loaded PEGylated and stearic acid grafted chitosan oligosaccharide micelle solution and Doxorubicin were respectively added to the wells, and the untreated blank cells were used as control. A repeated well of each above group was set. The cells were cultured in normal DMEM medium for 48. After 20 μL of 5 mg/mL methylthiazoletetrazolium (MTT) solution was added to each well, the cells was re-cultured in 37° C., 5% CO$_2$ incubator for 4 h, and then the supernatant was discarded. By adding 150 μL dimethyl sulfoxide to each well, a multi-functional microplate reader was used to measure the absorbance, and then the cell inhibition ratio was calculated according to the following formula:

Cell inhibition ratio %=(absorbance of control group−
absorbance of experimental group)/absorbance of
control group×100%

By calculation, the $IC_{50}$ values (50% inhibiting concentration) of PEGylated and stearic acid grafted chitosan oligosaccharide, doxorubicin solution and drug-loaded PEGylated and stearic acid grafted chitosan oligosaccharide micelle solution on MCF-7 and its drug-resistant cell MCF-7-adr were summarized in table 4.

TABLE 4

| | $IC_{50}$ (µg/mL) | |
|---|---|---|
| | MCF-7 | MCF-7-adr |
| PEGylated and stearic acid grafted chitosan oligosaccharide | 435.3 | 378.8 |
| Doxorubicin hydrochloride solution | 0.48 | 24.8 |
| Drug-laded PEGylated and stearic acid grafted chitosan oligosaccharide | 0.28 | 0.30 |

The above results suggested that the PEGylated and stearic acid grafted chitosan oligosaccharide of present invention was the material with low cytotoxicity, and after adriamycin was encapsulated by PEGylated and stearic acid grafted chitosan oligosaccharide micelle, the antitumor efficacy on sensitive MCF-7 cells could be increased by 1 time, and the drug resistance of its drug-resistant cell could be completely reversed.

(b) Paclitaxel Preparation

The same method in the above (4.1) (c) was used to prepare paclitaxel-loaded PEGylated and stearic acid grafted chitosan oligosaccharide micelle.

By determination, the particle diameter of PEGylated and stearic acid grafted chitosan oligosaccharide micelle was 85.6 nm and the surface potential was 32.5 mV. Drug encapsulation efficiency was 98.5%.

Subsequently, the inhibition ratio of tumor cells was used to evaluate the antitumor efficacy of drug-loaded PEGylated and stearic acid grafted chitosan oligosaccharide and the reversal efficiency of drug resistance of drug-resistant tumor cells.

Specifically, the ovarian cancer cell SKOV-3 and its drug-resistant cell SKOV-3/ST30 used as the model cells were cultured in 96-well culture plate. 100 µL culture solution containing $5 \times 10^3$ SKOV-3 or SKOV-3/ST30 cells was added to each well and cultured for 24 h in 37° C., 5% $CO_2$ incubator. After the cells completely adhered to the plate, different concentrations of drug-loaded PEGylated and stearic acid grafted chitosan oligosaccharide micelle solution and taxol solution were respectively added to the wells, and the untreated blank cells were used as control. A repeated well of each above group was set. The cells were cultured in normal DMEM medium for 48. After 20 µL of 5 mg/mL methylthiazoletetrazolium (MTT) solution was added to each well, the cells was re-cultured in 37° C., 5% $CO_2$ incubator for 4 h, and then the supernatant was discarded. By adding 150 µL dimethyl sulfoxide to each well, a multi-functional microplate reader was used to measure the absorbance, and then the cell inhibition ratio was calculated according to the following formula:

Cell inhibition ratio %=(absorbance of control group−
absorbance of experimental group)/absorbance of
control group×100%

By calculation, the $IC_{50}$ values of taxol solution and drug-loaded PEGylated and stearic acid grafted chitosan oligosaccharide micelle solution on SKOV-3 and its drug-resistant cell were summarized in table 5.

TABLE 5

| | $IC_{50}$(µg/mL) | |
|---|---|---|
| | SKOV-3 | SKOV-3/ST30 |
| Taxol solution | 0.45 ± 0.05 | 10.25 ± 0.23 |
| drug-loaded PEGylated and stearic acid grafted chitosan oligosaccharide | 0.10 ± 0.02 | 0.14 ± 0.03 |

These results suggested that after paclitaxel was packaged by PEGylated and stearic acid grafted chitosan oligosaccharide micelle, the antitumor efficacy on sensitive cells of ovarian cancer cell SKOV-3 could be increased by 3.5 times, and the drug resistance of the drug-resistant cell of ovarian cancer could be completely reversed.

(6) Application of PEGylated and Fatty Acid Grafted Chitosan Oligosaccharide in Pharmaceutical Composition for Gene Therapy (a) Plasmid DNA Preparation Preparation of Plasmid DNA-Loaded PEGylated and Fatty Acid Grafted Chitosan Oligosaccharide Micelle 10 mg PEGylated and fatty acid grafted chitosan oligosaccharide prepared in embodiment 8 (the molecular weight of PEG is 2,000 Da; the molecular weight of chitosan oligosaccharide is 18,600 Da; the grafting ratio of PEG was 8.1%; the grafting ratio of stearic acid was 48.3%) was precisely weighed, dissolved in 10 mL water, and prepared into micelle solution. After treated by water bath sonication for 15 min, the solution was filtered with 0.22 µm microporous membrane for sterilization. pEGFP (Green fluorescent protein plasmid DNA) solution (500 µg/mL) was prepared with 25 mM $Na_2SO_4$ solution. The micelle solution and green fluorescent protein plasmid DNA solution were mixed with the N/P ratio (the molar ratio of amino group of chitosan oligosaccharide to phosphate group of DNA) of 3, followed by standing at room temperature for 25 min to further promote the formation of micelle/plasmid DNA composite nanoparticles.

The appropriate amount of mixed suspension was properly diluted with deionized water, and then the particle size and surface potential were measured by particle size and surface potential analyzer. The physical and chemical properties of plasmid DNA-loaded PEGylated and fatty acid grafted chitosan oligosaccharide were shown in Table 6.

TABLE 6

| Particle diameter of control micelle (nm) | Particle diameter of pEGFP (nm) | Particle diameter of CSO-SA/pEGFP (nm) | Surface potential (mv) |
|---|---|---|---|
| 87.2 | 25.3 | 128.1 | 32.1 |

These results showed that, when composite micelle of the graft micelle and pEGFP DNA was formed, the particle size has been increased, indicating that formation of the composite micelle was achieved through the package and adherence of pEGFP plasmid DNA with a plurality of graft micelles.

Transfection of pEGFP Gene-Loaded Graft Micelle in Cells

Culture of A549 Cells

The human typeII pulmonary epithelial cells A549 were continuously cultured in the medium supplemented with 10% calf serum (5% CO2, 37° C. incubator). Subsequently, the cells during logarithmic growth phase were trypsinized and then diluted with DMEM. The diluted cells were inoculated into 24-well culture plates with the inoculum density of $2\times10^5$ per well, and pre-cultured in incubator for 24 h.

In Vitro Transfection of Graft-pEGFP Micelle

The A549 cells were inoculated into 24-well cell culture plate with the inoculum density of $2\times10^5$ per well 24 h prior to transfection, and then re-cultured in 37° C., 5% $CO_2$ incubator till 80-90% of the cells were fused. Before transfection, the old culture medium in plate was removed. After the cells were washed twice with PBS, the liposome Lipofectamine™2000, graft-pEGFP composite nanoparticles suspension and appropriate serum-free DMEM medium of which pH had been adjusted to 7.4 were added to the cells to the final volume of 0.5 ml; after culture for 6 h, the medium was substituted by complete medium, followed by re-culture for 72 h.

Determination of transfection efficiency: after removing the culture medium, the cells were washed twice with PBS, digested, and dispersed with a certain amount of PBS. The transfection efficiency was measured with flow cytometry. The results showed that the cell transfection efficiency mediated by graft (N/P58) was 14.2%, and the transfection efficiency mediated by liposome Lipofectamine™2000 was 25.1%

In Vivo Gene Therapy Using pEDF Gene-Loaded Graft Micelle

PEDF was taken as the theoretical gene, and the drug-loaded graft micelle was prepared. Nude mouse with QGY tumor as the animal model was administered twice (on the $1^{st}$ and $5^{th}$ day respectively) with 2.5 mg/kg plasmid DNA (with carrier volume 7.5 mg/kg) once; 21 days later, the tumor inhibition ratio of the animal model with QGY tumor could reach 49.04% (the treatment of successive administration for 7 days with 2 mg/kg adriamycin once was conducted as positive control, and the tumor inhibition ratio of 78.85% was obtained at last).

(b) siRNA Preparation

Preparation of siRNA-Loaded PEGylated and Fatty Acid Grafted Chitosan Oligosaccharide Micelle 10 mg PEGylated and fatty acid grafted chitosan oligosaccharide (the molecular weight of PEG is 2,000 Da; the molecular weight of chitosan oligosaccharide is 18,600 Da; the grafting ratio of PEG was 8.1%; the grafting ratio of stearic acid was 48.3%) was dissolved in 10 mL water to be prepared into micelle solution. After treated by water bath sonification for 15 min, the solution was filtered with 0.22 μm microporous membrane for sterilization. And the siRNA solution (500 μg/mL) was prepared with 25 mM $Na_2SO_4$ solution. The micelle solution and siRNA solution were mixed with the N/P ratio of 3, followed by standing at room temperature for 25 min to further promote the formation of micelle/siRNA composite nanoparticles.

The appropriate amount of mixed suspension was properly diluted with deionized water, and then the particle size and surface potential were measured by particle size and surface potential analyzer. The physical and chemical properties of siRNA-loaded PEGylated and fatty acid grafted chitosan oligosaccharide were shown in Table 7.

TABLE 7

| Particle diameter of control micelle (nm) | Particle diameter of siRNA (nm) | Particle diameter of CSO-SA/siRNA (nm) | Surface potential (mV) |
|---|---|---|---|
| 87.2 | 24.2 | 108.0 | 27.8 |

(7) Application of PEGylated and Stearic Acid Grafted Chitosan Oligosaccharide in Antiviral Drug Composition Preparation of Antiviral Drug-Loaded PEGylated and Stearic Acid Grafted Chitosan Oligosaccharide Micelle 100 mg PEGylated and stearic acid grafted chitosan oligosaccharide prepared in embodiment 8 (the molecular weight of PEG is 2,000 Da; the molecular weight of chitosan oligosaccharide is 18,600 Da; the grafting ratio of PEG was 8.1%; the grafting ratio of stearic acid was 48.3%) was placed in 50 mL breaker, and then treated with ultrasonic probe for 20 times (500 w, stimulation time 2 s and intermission time 3 s) by adding 90 mL distilled water (pH 5.7). Subsequently, the solution was transferred into a volumetric flask to set the total volume to 100 mL with distilled water, and then 1 mg/mL micelle solution was obtained. 20 mL of the PEGylated and stearic acid grafted chitosan oligosaccharide micelle solution was taken and added with 1 mL 1 mg/mL adefovir, acyclovir, adefovir dipivoxil, entecavir and ganciclovir solutions respectively. After stirred at room temperature for 3 h, they were treated with ultrasonic probe for 20 times (500 w, stimulation time 2 s and intermission time 3 s), and filtered with 0.22 μm microporous membrane, then the antiviral drug-loaded PEGylated and stearic acid grafted chitosan oligosaccharide micelles were obtained.

The particle size and surface potential of drug-loaded micelles were measured by the particle size and surface potential analyzer, and drug encapsulation efficiency was measured by HPLC. The physical and chemical properties of antiviral drug-loaded PEGylated and stearic acid grafted chitosan oligosaccharide were shown in Table 8

TABLE 8

| Drugs | Particle diameter of drug-loaded micelle (nm) | Surface potential of drug-loaded micelle (mV) | Drug entrapment efficiency (%) |
|---|---|---|---|
| Adefovir | 108.6 | 39.0 | 27.8 |
| Aciclovir | 110.4 | 32.7 | 25.7 |
| Adefovir dipivoxil | 98.8 | 33.5 | 34.9 |
| Entecavir | 101.5 | 34.2 | 29.3 |
| Ganciclovir | 108.4 | 36.8 | 25.7 |

Antiviral Activity of PEGylated and Stearic Acid Grafted Chitosan Oligosaccharide Micelle HepG2.2.15 cells were cultured in RPMI 1640 medium supplemented with about 10% calf serum (in 5% $CO_2$, 37° C. incubator). The cells were incubated as they entered into logarithmic growth phase. Specifically, the cells in logarithmic growth phase were washed with PBS, trypsinized and diluted with culture medium. Then the diluted cells were inoculated into 24-well culture plate with the inoculum density of $1\times10^4$ per well, followed by culture for 24 h in incubator till the cells adhered to the plates. After removing the old culture medium, the cells were washed twice with buffer solution (PBS) at PH7.4, and different concentrations of adefovir solution and adefovir-loaded PEGylated and stearic acid grafted chitosan oligosaccharide micelle were added. The cells were re-cultured for 2, 4, 6, 8 and 10 days. Finally, the culture medium was collected and used to detect the surface antigen (HBsAg) and e antigen (HBeAg) levels with enzyme immunoassay kit, to measure hepatitis B virus DNA (HBV DNA) content with real-time quantitative PCR method, to determine the cell survival rate with MTT Assay.

Figure 4A:
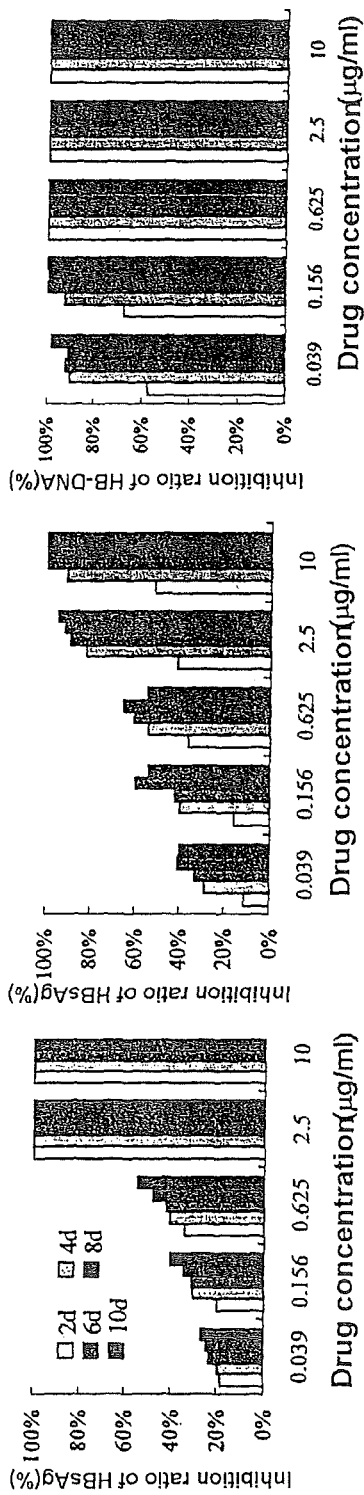
FIGS. 4A and 4B show inhibitory effect the pharmaceutical compositions comprising the PEGylated and stearic acid grafted chitosan oligosaccharide as a carrier of the present invention and a drug solution as the control on expression of HBsAg, HBeAg and HBV-DNA (after co-incubation with HepG2.2.15 cells), respectively.
Figure 4B:
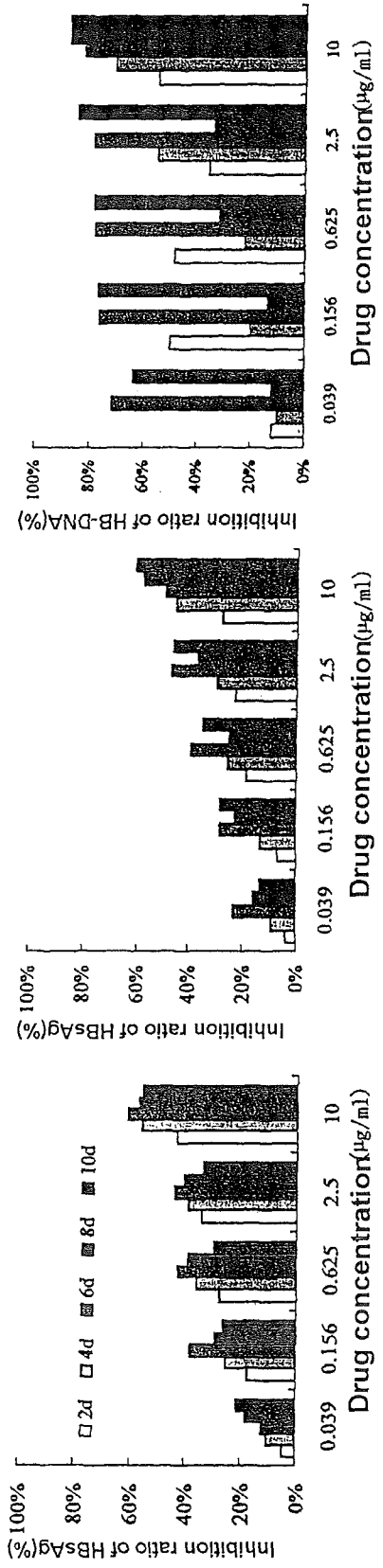

After adefovir dipivoxil and drug-loaded PEGylated and stearic acid grafted chitosan oligosaccharide micelle were incubated with HepG2.2.15 cells, their effects on the inhibition ratio of HBsAg, HBeAg and HBV-DNA expression were shown in FIGS. 4A and 4B.

The results revealed that adefovir dipivoxil loaded graft micelle could significantly increase the antiviral effect of the drugs; particularly, the inhibitory effect on the expression of hepatitis B virus DNA was so significant that the hepatitis B virus DNA expression can be completely inhibited by a lower dose of it.

Therapeutic index (TI) is one of the indices to evaluate the prospect of clinical application of antiviral drugs. TI>2 means effective and low toxic, 1<TI<2 represents low efficiency and toxical, TI<1 means toxic effect. $TI=TC_{50}/IC_{50}$, wherein $TC_{50}$ refers to the drug concentration causing 50% cell death on the $10^{th}$ day after the virus-infected cells was treated with drugs, which can be determined by the methods known in the art; $IC_{50}$ refers to the drug concentration reaching 50% inhibition ratio on HBsAg and HbeAg on the $10^{th}$ day after the virus-infected cells was treated with drugs. The therapeutic index of adefovir dipivoxil-loaded graft micelle delivery system on HBsAg and HBeAg were shown in Table 9.

TABLE 9

|  | $TC_{50}$ (μg/mL) | $IC_{50}$ (μg/mL) | TI |
|---|---|---|---|
| HBsAg | 1.13 | 0.472 | 2.4 |
| HBeAg | 1.13 | 0.121 | 9.3 |

The result suggested that the therapeutic index of adefovir dipivoxil-loaded graft micelle delivery system on HBsAg and HBeAg were all greater than 2, indicating that the antiviral drug composition using the PEGylated and stearic acid grafted chitosan oligosaccharide of the invention as the carrier is high-efficiency and low toxical antiviral preparation.

Industrial Application

The PEGylated and stearic acid grafted chitosan oligosaccharide of the invention can be widely used as a drug carrier in a variety of pharmaceutical compositions, which can not only improve the targeting absorption of drug active ingredients in vivo, but also prevent the drugs from decomposition to some extent, thereby maintaining the stability of drugs and reducing drug side effects. Therefore, the PEGylated and stearic acid grafted chitosan oligosaccharide and the pharmaceutical compositions comprising the graft of the invention can be widely applied in industry.

The invention claimed is:

1. A PEGylated and fatty acid grafted chitosan oligosaccharide comprising a structural unit represented by the following Formula (I) and a structural unit represented by the following Formula (II),

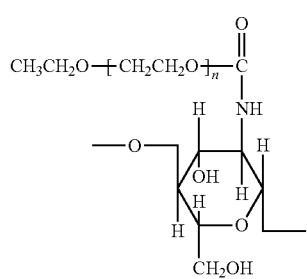

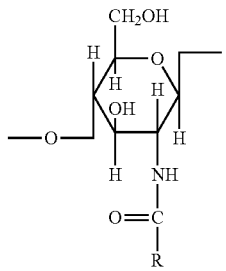

wherein part of free amino groups of chitosan oligosaccharide chain are replaced by a fatty acid having 12-22 carbon atoms or a PEG having a molecular weight of 1,000-10,000 Da, where n refers to degree of polymerization of the PEG, and R is an alkyl group having 11-21 carbon atoms; and the grafting ratio of fatty acids is 1%-50%, and the grafting ratio of the PEG is 0.05%-50%.

2. The PEGylated and fatty acid grafted chitosan oligosaccharide according to claim 1, wherein the grafting ratio of the PEG is 0.5%-50%.

3. The PEGylated and fatty acid grafted chitosan oligosaccharide according to claim 1 or 2, wherein the grafting ratio of fatty acids is 5%-50%.

4. The PEGylated and fatty acid grafted chitosan oligosaccharide according to claim 1, wherein the PEG has a molecular weight of 2,000-10,000 Da.

5. The PEGylated and fatty acid grafted chitosan oligosaccharide according to claim 1, wherein the fatty acid is at least one selected from the group consisting of lauric acid, myristic acid, palmitic acid, oleic acid, stearic acid and docosanoic acid.

6. A method for preparing the PEGylated and fatty acid grafted chitosan oligosaccharide according to claim 1, comprising the following steps:
(a) degrading a chitosan in the presence of an enzyme to obtain a chitosan oligosaccharide having a molecular weight of less than 200,000 Da;
(b) coupling the chitosan oligosaccharide with a fatty acid having 12-22 carbon atoms in the presence of a crosslinking coupling agent to obtain a fatty acid grafted chitosan oligosaccharide; and
(c) coupling a terminal-substituted PEG with the fatty acid grafted chitosan oligosaccharide to obtain the PEGylated and fatty acid grafted chitosan oligosaccharide, wherein the molecular weight of the PEG is 1,000-10,000 Da.

7. The method according to claim 6, wherein in the steps (c), the molar ratio of the terminal-substituted PEG to the fatty acid grafted chitosan oligosaccharide is 1:20-80:1.

8. The method according to claim 6, wherein the terminal-substituted PEG is selected from the group consisting of terminal-aldehydated PEG, terminal-carboxylated PEG, terminal-succinimidated PEG and terminal-maleic anhydridated PEG.

9. A pharmaceutical composition comprising a pharmaceutically active ingredient and the PEGylated and fatty acid grafted chitosan oligosaccharide according to claim 1.

10. The pharmaceutical composition according to claim 9, wherein the pharmaceutically active ingredient is an antitumor drug.

11. The pharmaceutical composition according to claim 10, which is capable to of reversing drug resistance of tumor cells.

12. The pharmaceutical composition according to claim 9, wherein the pharmaceutically active ingredient is a gene therapy drug.

13. The pharmaceutical composition according to claim 9, wherein the pharmaceutically active ingredient is an antiviral drug.

14. The pharmaceutical composition according to claim 13, wherein the anti-hepatitis B virus drug is at least one selected from the group consisting of adefovir, acyclovir, adefovir dipivoxil, entecavir and ganciclovir.

15. A method of preparing a pharmaceutical composition comprising a step of combining the PEGylated and fatty acid grafted chitosan oligosaccharide according to claim 1 with a pharmaceutically active ingredient.

16. The method according to claim 15, wherein the pharmaceutical composition comprises an antitumor drug, a gene therapy drug or an antiviral drug.

17. The pharmaceutical composition according to claim 10, wherein the anititumor drug is at least one selected from the group consisting of mitomycin C, doxorubicin, paclitaxel and hydroxycamptothecin.

18. The pharmaceutical composition according to claim 12, wherein the gene therapy drug is plasmid DNA or siRNA.

19. The pharmaceutical composition according to claim 13, wherein the antiviral drug is an anti-hepatitis B virus drug.

* * * * *